United States Patent
Zhang et al.

(10) Patent No.: US 9,650,424 B2
(45) Date of Patent: May 16, 2017

(54) PORCINE PSEUDORABIES VIRUS, VACCINE COMPOSITION AND PREPARATION METHOD AND USE THEREOF

(71) Applicant:

(51) Int. Cl.

| | |
|---|---|
| *C07K 14/005* | (2006.01) |
| *C07H 21/04* | (2006.01) |
| *C12N 7/04* | (2006.01) |
| *A61K 39/12* | (2006.01) |
| *A61K 39/245* | (2006.01) |
| *A61K 39/00* | (2006.01) |

(52) U.S. Cl.
CPC .......... *C12N 7/00* (2013.01); *C12N 7/04* (2013.01); *A61K 39/00* (2013.01); *A61K 2039/5252* (2013.01); *A61K 2039/552* (2013.01); *C12N 2710/16721* (2013.01); *C12N 2710/16722* (2013.01); *C12N 2710/16734* (2013.01); *C12N 2710/16761* (2013.01); *C12N 2710/16771* (2013.01)

(56) References Cited

U.S. PATENT DOCUMENTS

| | | | |
|---|---|---|---|
| 5,738,854 A * | 4/1998 | Mettenleiter | C07K 14/005 424/199.1 |
| 6,255,078 B1 | 7/2001 | Petrovskis et al. | |

FOREIGN PATENT DOCUMENTS

| | | | |
|---|---|---|---|
| CN | 102952785 A | | 3/2013 |
| CN | 102994458 A | | 3/2013 |
| CN | 104459121 A | * | 3/2015 |

OTHER PUBLICATIONS

Ye et al., "Genomic characterization of emergent pseudorabies virus in China reveals marked sequence divergence: Evidence for the existence of two major genotypes," Virology 483: 32-43 (2015).*

Yang et al., "Pathogenicity of a currently circulating Chinese variant pesudorabies virus in pigs," World J. Virol 5(1): 23-30 (2016).*

Lytle et al., "Predicted Inactivation of Viruses of Relevance to Biodefense by Solar Radiation," J. Virol. 79(22):14244 (2005).*

Zhong et al. (GenBank Accession No. KC981239.1, "Suid herpesvirus 1 strain BJ/YT Genome")(2013).*

Chinese Office Action dated Aug. 28, 2015, in connection with corresponding CN Application No. 201410241279.2 (24 pgs., including English translation).

Chinese Office Action dated Jan. 13, 2016, in connection with corresponding CN Application No. 201410241279.2 (12 pgs., including English translation).

Chen, Zhenhai et al.; "Cloning and Sequence Analysis of gB, gC, gD Genes of Pseudorabies Virus Strain Fa"; Fujian Journal of Agricultural Sciences; vol. 22, No. 2, Dec. 31, 2007; pp. 120-125; Abstract attached; Cited in ISR of corresponding PCT/CN2014/076691.

International Search Report dated Jul. 29, 2014 from corresponding International Application No. PCT/CN2014/076691; 6 pages.

* cited by examiner

Fig. 1

```
Majority       MASLARAMLALLALYTAAIAAAPSSTTALGTTPNGGGGGNSSAGELSPSPPSTPEPVSGTTGAAASTPAAVSTPVVPPPSVSPRKPQRNGNRTRVHGLKA
                        10        20        30        40        50        60        70        80        90       100

HN1201 gC pro.pro  MASLARAMLALLALYTAAIAAAPSSTTALGTTPNGGGGGNSSAGELSPSPPSTPEPVSGTTGAAASTPAAVSTPRVVPPPSVSPRPKPQRNGNPTRVRGDKA 100
gC SA215 pro.pro   .............H.........................................V..........D.........E..... 100

Majority       TSHGRKRIVCRERLFSARVGDAVSPGCAVVTPRAGETFEVRFSYRRGRFRSVTADPEYFDEPPRYELPRERLLFSSAMASLAHADALASAVVEGERATVAM
                       110       120       130       140       150       160       170       180       190       200

HN1201 gC pro.pro  TSHGPKRIVCREPLFSAPVGDAVSFGCAVVTPRAGETFEVRFCRRGPFRSPDADPEYFDEPPFPPELPREPLLFSSANASLAHADALASAVVEGEPATVAM 200
gC SA215 pro.pro   ...R......................................R........................................ 200

Majority       VSGEVSVRVAAADAETEGVYTWRVLSANGTEVRSANVSLVLYSQPEFGLSAPPVLFGEPFPAVCYVRLYYPRRSVRLRWFADEHPVDAAFYTNSTVADEL
                       210       220       230       240       250       260       270       280       290       300

HN1201 gC pro.pro  VSGEVSVRVAAADAETEGVYTMRVLSANGTEVRSANVSLVLYSQPEFGLSAPPVLFGEPFRAVCVVRDYYPRRSVRLPWFADEHPVDAAFYTNSTVADEL 300
gC SA215 pro.pro   ...S................................................................................. 300

Majority       GRRTPVSVVNVTPADVPGLAAADDADALAPSLRCEAVMYRDSVASQRFSEALRPHVYHPAAVSYRFVEGFAVCDGLCVPPEARLAWSDHAADTVYRLGAC
                       310       320       330       340       350       360       370       380       390       400

HN1201 gC pro.pro  GPRTRPSVVNPTRADVPGLAAADCADALAPSLSCEAVMYTDSVASQRFSEALRPHVYHPAAVSVRFVEGFAVCDGLCVPPEARLAWSDHAADTVYRLGAC 400
gC SA215 pro.pro   ............................................................................................... 400

Majority       AEHPGLLNVPSAPPLSDLDGPVDYTYICRLEGHPSQLPVFEDTQRYDASPTZVSNPVVTVRMTIVIAGIAILAILVYIHATCVVYPRAGL--
                       410       420       430       440       450       460       470       480

HN1201 gC pro.pro  AEHPGLLNVPSAPPLSDLDGPVDYTYCRLEGHPSQLPIFEDTQRYDASFTSVSNPVVTSMITVLAGTAILAIVLVIRATCVYYPRAGFK 428
gC SA215 pro.pro   ...........I................................................................SYL 483
```

*Note: HN1201 gC pro.pro : SEQ ID NO: 3     gC SA215 pro.pro: SEQ ID NO: 7

Fig. 2

```
Majority       MLLAALLAALVAPTTLGADVTAVPAPTFPPPAYPYTESWQLTLTTVPSPFVGPADVYHTRPLEDPCGVVALISDLQVLRLLNEAVAHRPTYRAHVANVRIADGC
                        10        20        30        40        50        60        70        80        90       100

HN1201 gD pro.pro  MLLAALLAALVAPTTLGADVDAVPAPTFPPPAYPYTESWQLTLTTVPSPFVGPADVYHTRPLEDPCGVVALISDIQVDRLLNEAVAHRRPTYPANVANVRKAIGC 105
gD SA215 pro.pro   ...................................................E...........................S........... 105

Majority       AHLLYFIEYADCDPRGIFGRCRRPTTPMVWTPSADYMFPTEDELGLLMPAPGPFNESQTRRLVSVDGVNILTDFMVALPEGQECPFARVDQHRTYRFDACWSDRS
                       110       120       130       140       150       160       170       180       190       200       210

HN1201 gD pro.pro  AHLLYFIEYADCDPRGIFGRCRRTTPMWWTPSADYRFPTEDELGLLMVAPGPFKEGQYRRLVSVDGVNILTDFMVALPEGQECPFAPVDQHRTYRFRGACSSDDS 210
gD SA215 pro.pro   ..................................................................................................... 210

Majority       FKRGVLVRPFLTPFYQQPPHREVVMYWYRKNGRTLPRAYAAATPYAILPARPSAGSPRPRPRPRPEPEPRPKPEPAPATPAPPGRLPEPATPDHAAGGRPTPRPRP
                       220       230       240       250       260       270       280       290       300       310

HN1201 gD pro.pro  FKRGVLVRPFLTPFYQQPPHREVVMYWYRKNGRTLPRAYAAATPYAIDPARPSAGSPRPRPRPRPPEPEPAPATPAPPGRLPEPATRDHAAGGRPTPRPRP 315
gD SA215 pro.pro   ............................................................................................. 315

Majority       ETPHRPFAPPAVVPSGWPQPAEPFPPRTTAAPEVSRHPSVIVGTGTAMGALLVGVCVYIPFRLRGAKGYRLLGGPADADELKAQPGP--
                       320       330       340       350       360       370       380       390       400

HN1201 gD pro.pro  ETPHRPFAPPAVVPSGWPQPAEPFPPRTTAAPGVSRHRSVIVCTGTAMSGALLVGVCVYIFFRLRGAKGYRLLGGPADADELKAQPGPI 403
gD SA215 pro.pro   ................................................................................... 403
```

*Note: HN1201 gD pro.pro : SEQ ID NO: 1     gD SA215 pro.pro: SEQ ID NO: 8

PORCINE PSEUDORABIES VIRUS, VACCINE COMPOSITION AND PREPARATION METHOD AND USE THEREOF

REFERENCE TO A SEQUENCE LISTING

This application incorporates-by-reference nucleotide and/or amino acid sequences that are present in the file named "170330_89396—A_Substitute_Sequence_Listing.txt" which is 31.9 kilobytes in size, and which was created Mar. 27, 2017 in the IBM-PC machine format, having an operating system compatibility with MS-Windows, which is contained in the text file filed Mar. 30, 2017 as part of this application.

FIELD OF THE INVENTION

This invention relates to a vaccine composition, belonging to the field of animal virology.

BACKGROUND

Pseudorabies, also called Aujeszky's disease, is an acute infectious disease caused by Suid herpesvirus 1 (SuHV1) belonging to the Alphaherpesvirinae subfamily for many kinds of livestock such as swine, cattle and sheep, as well as poultry and wild animals, with the main symptoms of fever, intense itching (except swine) and encephalomyelitis. Pseudorabies in swine is found nationwide in China causing severe damages, and is one of the major diseases limiting the large-scale production of pig farms. Infection can result in abortion, stillborn or mummified fetuses in pregnant sows, and neurological signs, paralysis and a high death rate in piglets. Pseudorabies virus (PRV) with strong pantropic properties, neurotropic properties and latent infectivity, may establish long-term latent infection in the peripheral nervous system, and then the latently infected host starts to get sick when the latent virus is activated into the infectious virus.

It has been indicated by many researches that a corresponding protection can be provided for the vaccinated animals by a subunit vaccine, which is a vaccine prepared by cloning the protective antigen genes of pathogen into prokaryote and eukaryote expression systems with methods of genetic engineering so as to highly express those genes. It has been found so far that either of glycoprotein B, C and D (gB, gC and gD) in the PRV glycoproteins can make the body generate neutralizing antibodies, which have the ability to neutralize PRV, no matter in vivo or in vitro, or no matter with the presence or absence of complements. The article, Progress in Subunit Vaccine against Pseudorabies Virus Development (Chenghuai Yang, Gaoming Lou, Nanhui Chen, *Jiangxi Journal of Animal Husbandry & Veterinary Medicine* 2004 Issue 3) has disclosed that either of gB, gC and gD among 11 PRV glycoproteins which have been found so far, can induce the body to generate neutralizing antibodies. In the absence of complements, monoclonal antibodies directed against gB, gC and gD can neutralize PRV. The swine and mice injected with monoclonal antibodies directed against gB, gC and gD can resist attacks by virulent PRV strains. Therefore gB, gC and gD are the most preferred proteins for developing PRV subunit vaccine. The glycoprotein, gD, is an important neutralizing antigen as well as the main target for protective antibodies, and it can induce better protective response. As disclosed by U.S. Pat. No. 6,858,385 and U.S. Pat. No. 6,521,231, vaccine for preventing pseudorabies can be prepared by use of gD of porcine pseudorabies virus.

The porcine PRV has only one serotype, thus usually the cross-protection immunity between strains of porcine PRV is considered to be very strong. However, piglets may still suffer from typical porcine pseudorabies after their injection with commercial vaccines, with symptoms such as long-term high fever, depression, loss of appetite, respiratory and/or neurological signs. The significant manifestations include that infection among swine at any ages, horizontal transmission among swine herds, short incubation period (1~2 days), morbidity rates between 10%~100%, mortality rate in pigs between 10%~100% (mortality rate in piglets can reach up to 100%), high fever in pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and the infection also can cause reproductive disorder symptoms such as declined semen quality of boar, as well as abortion of pregnant sow (the abortion rate can reach up to 35%), premature birth, stillbirth, weakened piglets (weakened piglets die by 14 days of age), etc. By means of prior art, vaccinated pigs cannot completely resist attacks by the wild virus, and still have symptoms like high fever, depression, partially or completely loss of appetite, with a infection rate of more than 30% and a mortality rate between 10% and 20%. There are no vaccines in the prior art capable of solving the pseudorabies caused by variant strains of porcine pseudorabies virus.

SUMMARY OF INVENTION

In order to solve the deficiency of the prior art, the present invention aims to provide a porcine pseudorabies virus strain for preparing vaccines, which have been proved by animal testing to provide a good immune function for porcine pseudorabies.

The present invention provides a nucleotide sequence substantially encoding the protein as shown in SEQ ID NO. 1 of the sequence listing.

The present invention provides a nucleotide sequence substantially encoding the protein as shown in SEQ ID NO.2 of the sequence listing.

The present invention provides a nucleotide sequence substantially encoding the protein as shown in SEQ ID NO. 3 of the sequence listing.

The "nucleotide sequence" in the present invention refers to a deoxyribonucleic acid (DNA) sequence, which can be transcribed into a corresponding RNA sequence.

To solve the deficiency of the prior art, the main aim of present invention is to provide a porcine pseudorabies virus strain comprising gD glycoprotein encoded by the nucleotide sequence as shown in SEQ ID NO.4 of the sequence listing.

The term "gD glycoprotein" in the present invention refers to a structural protein required for infection of PRV, which is one of the major glycoproteins in the surface of envelope of mature virus particles, also called gp50 protein.

The term "homology" in the present invention refers to the level of similarity between two amino acid sequences or two nucleotide sequences. The homology between amino acid sequences or nucleotide sequences can be calculated by any appropriate methods well known in the art, for example, the target amino acid (or nucleotide) sequence and the reference amino acid (or nucleotide) sequence is aligned, and gaps can be induced if necessary to optimize the number of the identical amino acids (or nucleotides) between two aligned sequences, and the percentage of the identical amino acids (or nucleotides) between two aligned sequences can be calculated accordingly Alignment of amino acid (or nucleotide) sequences and calculation of homology can be achieved by software well known in the art. Examples of such software include, but is not limited to, BLAST (which can be accessed through the website of the National Center for Biotechnology Information, NCBI, or can be found in Altschul S. F. et al, J. Mol. Biol, 215:403-410 (1990); Stephen F. et al, Nucleic Acids Res., 25:3389-3402(1997)), ClustalW2 (which can be accessed through the website of the European Bioinformatics Institute, EBI, or can be found in Higgins D. G. et al, Methods in Enzymology, 266:383-402(1996); Larkin M. A. et al, Bioinformatics (Oxford, England), 23 (21):2947-8 (2007)), and TCoffee (which can be accessed through the website of the Swiss Institute of Bioinformatics, SIB, or can be found in, Poirot O. et al, Nucleic Acids Res., 31(13):3503-6(2003); Notredame C. et al, J. Mol. Boil, 302(1):205-17(2000)) etc. It is all within the knowledge scope of a person skilled in the art that when using the software to do sequence alignment, he can use the default parameters provided by the software or adjust the parameters provided by the software according to the actual condition.

Preferably, said PRV strain comprises the gB glycoprotein encoded by the nucleotide sequence shown in SEQ ID NO.5 of the sequence listing.

Preferably, said PRV comprises the gB glycoprotein encoded by the amino acid sequence as shown in SEQ ID NO.2 of the sequence listing.

Preferably, said PRV according to the invention comprises the gC glycoprotein encoded by the amino acid sequence as shown in SEQ ID NO.3 of the sequence listing.

Preferably, said PRV strain is HN1201 strain (pseudorabies virus, strain HN1201), or culture thereof, of which the accession number is CCTCC NO. V 201311; the HN1201 strain was deposited in the China Center for Type Culture Collection (CCTCC) on May 20, 2013, of which the address is Wuhan University, Wuhan City, Hubei Province.

The term "culture" refers to cultures of different passages of the virus, known to those skilled in the art, which may only have minute variations from one passage to another. Preferably said culture is a culture within 5~35 passages.

Another aim of the invention is to provide a vaccine composition comprising an immune amount of attenuated live vaccine, inactivated vaccine, subunit vaccine, synthetic peptide vaccine, or genetically engineered vaccine of said porcine pseudorabies virus strain.

Preferably the vaccine composition comprises an immune amount of attenuated live vaccine, inactivated vaccine, subunit vaccine, synthetic peptide vaccine, or genetically engineered vaccine of the said PRV HN1201 strain or culture thereof.

Preferably the vaccine composition according to the present invention comprises said PRV or antigen thereof as an active component. The PRV in the vaccine composition comprises gD glycoprotein represented by the amino acid sequence of SEQ ID NO. 1 or the amino acid sequence which shares at least 98% homology to the sequence of SEQ ID NO. 1.

Preferably the PRV in said vaccine composition is the HN1201 strain or culture thereof.

The antigen used in the invention is the antigen ingredients in the components of virus, which induces the immune response, and comprises gD protein with the amino acid sequence of SEQ ID NO. 1.

Optionally, the antigen may comprise gB protein with the amino acid sequence of SEQ ID NO. 2 or the one of which the fragment shares at least 95% homology to the sequence of SEQ ID NO. 2.

Optionally, the antigen may comprise gC protein with the amino acid sequence of SEQ ID NO.3 or the one of which the fragment shares at least 95% homology to the sequence of SEQ ID NO. 3.

As used herein, the term "live vaccines" refer to vaccines prepared by viruses which still can reproduce in the host or on the cells and in the meanwhile their virulence has been weakened. As used herein, the term "attenuated" refers to artificially reducing the virulence of pathogens via mutation of gene by preparing pathogens which are deprived of pathogenicity but maintain immunogenicity. Generally attenuation can be achieved by UV irradiation, chemical processing or continuous high-order subculturing in vitro. Artificial alteration of gene attenuates the virulence via, for example, the deletion of some specific nucleotides in the given sequence.

As used herein, the term "inactivated vaccine", also called non-living vaccine, refers to suspension of inactivated virus used as an antigen for producing immunity Examples of inactivated vaccines include whole virus vaccines and split virus vaccines. By using known methods it is easy to produce inactivated vaccines. For instance, one can obtain inactivated whole virus vaccines by treatment with formaldehyde solution. Split virus vaccines can be prepared with virus envelopes after treatment with ether.

The term "subunit vaccine" refers to a vaccine prepared via highly effectively expression of protective antigen gene of a pathogen by cloning it into a prokaryotic or eukaryotic expression system. A subunit vaccine has less risk of adverse reactions than a whole virus vaccine. For example, the expressed gD protein or gC protein of PRV can be used for preparing subunit vaccines.

The term "synthetic peptide vaccine" refers to a small peptide only comprising the component of immunogenic determinants, i.e. a vaccine prepared by synthesizing a protective short peptide according to the amino acid sequence of natural proteins, and adding in an adjuvant after connecting them to a carrier.

Preferably, said vaccine composition in the invention comprises an inactivated vaccine of the PRV HN1201 strain or culture thereof, of which the content is not less than $10^{6.0}TCID_{50}/ml$.

Preferably, said vaccine composition in the present invention may comprise $10^{6.0}TCID_{50}/ml$ PRV per pig. The vaccine cannot effectively trigger the generation of antibodies when the amount of said PRV used is less than $10^{6.0}TCID_{50}$. On the other hand the excessive amount may not be economical.

Preferably, said vaccine composition comprises 25~100 μg/dose of gD protein antigen of the PRV HN1201 strain or culture thereof.

In addition, said pseudorabies vaccine in the present invention can be used conjunctly with other inactivated pathogens or antigen to prepare combined vaccines or complex vacancies against various diseases including pseudorabies. As used herein, the term "combined vaccine" refers to a vaccine prepared with the virus mixture by mixing the pseudorabies virus in the present invention with at least one different virus. The term "complex vaccine" refers to a vaccine prepared from viruses and bacterium. For example, the pseudorabies virus in the present invention can be mixed or combined with classical swine fever virus, porcine reproductive and respiratory syndrome virus, porcine circovirus and/or *haemophilus parasuis* and *mycoplasma*.

Preferably, said vaccine composition further comprises medium, adjuvants and excipients.

Said vaccine composition according to the present invention also may comprise medium, adjuvants and/or excipients. Physiological saline or distilled water can be used as medium. Examples of adjuvants used in the vaccine composition include Freund's incomplete adjuvant or Freund's complete adjuvant, aluminum hydroxide gel, vegetable oil or mineral oil etc. Examples of excipients include, but are not limited to, aluminum phosphate, aluminum hydroxide and potassium aluminum sulfate. In practice, all substances for preparing vaccines, known to those skilled in the art, can be adapted to the vaccine composition in the present invention.

One more aim of the present invention is to provide a method for preparing said vaccine composition comprising the steps: the PRV HN1201 strain is amplified and cultured, inactivated, and then added with adjuvants and mixed thoroughly.

Specifically, the method comprises the steps: (1) inoculating the PRV vaccine strains into respective susceptible cells, and cultivating the inoculated susceptible cells; and then harvesting cell culture; and (2) treating the viruses obtained from step (1) with formaldehyde solution, BPL (β-beta-Propiolactone) or BEI (binary ethylenimine).

The susceptible cells can be continuous cell lines or primary cell lines. The susceptible cells adapted to PRV culture include but are not limited to continuous cell lines such as ST cell line (ATCC CRL-1746), PK-15 cell line (ATCC CCL-33), African green monkey kidney Marc-145 cell line (ATCC CRL-12219), Madin-Darby bovine kidney MDBK cell line (ATCC CCL-22), bovine turbinate BT cell line (ATCC CRL-1390), Vero cell line (ATCC CCL-81), BHK-21 cell line (ATCC CCL-10), pig kidney continuous cell line (such as IBRS-2, refer to e.g. DECASTRO, M.P.1964. Behavior of foot and mouth disease virus in cell culture: susceptibility of the IB-RS-2 swine cell line. Arquivos Instituto Biologica 31:63-78), rabbit kidney continuous cell line (RK, e.g. ATCC CCL-106) etc., and primary cell lines such as chicken embryo fibroblasts and porcine kidney cells etc. The primary cells can be isolated and prepared from tissues of animals via methods well known in the art.

The vaccine composition according to the present invention can be prepared into oral dosage forms or non-oral dosage forms. Non-oral dosage forms are preferred which can be administrated via intradermal route, intramuscular route, intraperitoneal route, intravenous route, subcutaneous route, intranasal route or epidural route.

Another aim of the invention is to provide a method for preparing the vaccine composition, comprising the steps: (1) cloning said PRV recombinant gD gene; (2) expressing said PRV recombinant gD protein; and (3) mixing said PRV gD protein antigen with adjuvants based on certain ratio and emulsifying the resulting mixture.

A further aim of the invention is to provide a use of said vaccine composition for preparing medicine for treatment and prevention of diseases relating to PRV.

As used herein, the term "diseases relating to PRV" can further refer to diseases caused by infection of PRV. Examples includes but are not limited to, obvious neurological signs, lethargy, crying, vomiting diarrhea and fever in infected piglets, and abortion, mummified or stillborn fetuses or reproductive disorder in infected pregnant sows.

As used herein, the term "diseases relating to PRV" can further refer to diseases with significant manifestations including but not limited to infection among swine at any ages, horizontal transmission among swine herds, short incubation period (1~2 days), morbidity rates between 10%~100%, mortality rate in pigs between 10%~100% (mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and reproductive disorder symptoms caused by infection such as declined semen quality of boar, as well as abortion of pregnant sow (the abortion rate can reach up to 35%), premature birth, stillbirth, weakened piglets (weakened piglets die by 14 days of age), etc. The differences between above described symptoms and symptoms caused by infection of regular pseudorabies virus in the prior art are: in adult pigs (whose weight is above 50 kg), high fever of infected pigs (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion; sudden incidence of pseudorabies in newborn piglets and piglets below the age of 4 weeks, further resulting in massive death with a mortality of more than 90%; main manifestations in infected piglets including increased body temperature over 41° C., completely loss of appetite, obvious neurological signs and diarrhea; and in piglets just before or after being weaned, mainly respiratory symptoms, such as dyspnea, coughing and runny noses, etc.

As used herein, the term "prevention" refers to all behaviors to inhibit the infection of pseudorabies virus or delay the onset of the disease via administration of the vaccine composition according to the present invention. The term "treatment" refers to all behaviors to relieve or cure the symptoms caused by infection of PRV via administration of the vaccine composition according to the present invention.

BRIEF DESCRIPTION OR THE DRAWINGS

FIG. 1. Result of homology analysis between amino acid sequences of gC in HN1201 strain and SA215 strain.

FIG. 2. Result of homology analysis between amino acid sequences of gD in HN1201 strain and SA215 strain.

SEQUENCE LISTING

SEQ ID NO. 1 is the amino acid sequence of gD in the PRV HN1201 strain.

SEQ ID NO. 2 is the amino acid sequence of gB in the PRV HN1201 strain.

SEQ ID NO. 3 is the amino acid sequence of gC in the PRV HN1201 s train.

SEQ ID NO. 4 is the nucleotide sequence of gD in the PRV HN1201 strain.

SEQ ID NO. 5 is the nucleotide sequence of gB in the PRV HN1201 strain.

SEQ ID NO.6 is the nucleotide sequence of gC in the PRV HN1201 strain.

SEQ ID NO. 7 is the amino acid sequence of gC in the PRV SA215 strain.

SEQ ID NO. 8 is the amino acid sequence of gD in the PRV SA215 strain.

SEQ ID NO. 9 is the nucleotide sequence of an upstream primer for amplifying gB gene.

SEQ ID NO. 10 is the nucleotide sequence of a downstream primer for amplifying gB gene.

SEQ ID NO. 11 is the nucleotide sequence of an upstream primer for amplifying gC gene.

SEQ ID NO.12 is the nucleotide sequence of a downstream primer for amplifying gC gene.

SEQ ID NO.13 is the nucleotide sequence of an upstream primer for amplifying gD gene.

SEQ ID NO.14 is the nucleotide sequence of a downstream primer for amplifying gD gene.

SEQ ID NO.15 is the nucleotide sequence of an upstream PRV gD-specific primer.

SEQ ID NO.16 is the nucleotide sequence of a downstream PRV gD-specific primer.

DETAILED DESCRIPTION

The description of the present invention is further provided as follows with reference to the specific embodiments, and features and advantages of the present invention will become more apparent from the following description. However, these embodiments are only exemplary, but not forming any limitation to the scope of the present invention. It should be understood by a person skilled in the art that modifications or alternatives to details and forms of the technical solution of the present invention without deviation from the spirit and scope of the present invention will be allowed, while those modification and alternatives should all fall within the scope of the present invention.

In the invention, the term "per pig" refers to the amount of vaccine each pig injected.

In the invention, the term "$TCID_{50}$" refers to 50% tissue culture infective dose, a way to represent viral infectivity.

Minimum Essential Medium (MEM) liquid medium is prepared with MEM dry powdered medium purchased from Life Technologies, Corp. according to the instruction.

Dulbecco's Modified Eagle's Medium (DMEM) in the present invention is prepared with reference to the preparation method from Appendix A of GB/T18641-2002 Diagnostic Techniques for Aujeszk's Disease.

In the present invention, the term "PBS" is the abbreviation for Phosphate Buffer Saline, and 0.01 mM pH 7.4 PBS as used in the present invention is prepared as described in *Molecular cloning: Laboratory manuals*, 3rd edition.

Example 1

Collection and Isolation of Viruses

Porcine brain tissue was collected under aseptic conditions from samples isolated from samples from Henan province suspected of having pseudorabies infection, added in MEM liquid medium in a ratio of 1:10(V:V), and ground to prepare a tissue suspension. After 3 times of repeated freezing-thawing, the tissue suspension was centrifuged at 2000 r/min for 15 minutes. The supernatant was then collected, filtered through a 0.2 μm pore filter, subcultured on PK-15 cells and incubated at 37° C. for 1 h, and then the medium was changed by adding MEM liquid medium supplemented with 2% fetal bovine serum, and incubated at 37° C. for 5 days. PRV was detected by PRV PCR detection kit (Beijing Anheal Laboratories Co., Ltd), and the result was positive; PCR kit was employed to detect the exotic virus contamination (porcine reproductive and respiratory syndrome virus RT-PCR detection kit kit, porcine parvovirus PCR detection kit and classical swine fever virus RT-PCR detection kit, all purchased from Beijing Anheal Laboratories Co., Ltd) for the isolated virus and the PCR detection result was negative, indicating a pure viral specie.

The isolated PRV strain was deposited in the China Type Culture Collection on May 20, 2013 named HN1201 strain (Pseudorabies virus, strain HN1201) of which the accession number is CCTCC NO. V 201311 and the preservation address is Wuhan University, Wuhan City, Hubei Province.

Example 2

Genetic Characteristics of the Isolated Virus

Genetic characteristics of the isolated virus in Example 1 were determined by means of gene analysis. Genomic DNA prepared from the pseudorabies virus isolated from PK-15 cells was used as template with primers shown in Table 1 for PCR amplification reactions. The Primer Primer 5.0 was used for designing the primer sequence for amplifying gB, gC and gD gene, respectively.

The genomic DNA extracted was used as template to prepare the following PCR amplification system: 100 μg template DNA, 0.5 μL, PrimerSTAR HS DNA Polymerase (2.5 U/μL), 250 μL 2× PrimerSTAR GC Buffer, 1 μL, of each upstream and downstream primer (10 pmol/μL), 4 μL dNTP Mix (2.5 mM each), adjusted to a final volume of 50 μL, with distilled water. Two-step PCR reaction was carried out by an initial denaturation for 10 sec at 98° C. followed by annealing and extension at 68° C. (all the time is calculated by 1 kb/min) and there were 30 cycles in total. The PCR reactions were finalized at 4° C. The analysis of the amplification products was conducted by electrophoresis on 1% agarose gel containing ethidium bromide. The sequences of PCR products were determined. The sequence data was analyzed by Lasergene.

TABLE 1

PCR primer sequences

| Target gene | Primer sequence (5'→3') | Size of PCR product |
|---|---|---|
| gB | aagcgcatctttattgtttcccg ggcttctaccgcttccagacgg | 2957 bp |
| gC | accgtcgccatgtgcgccacta cgggtcggactcgctgtcgtttatt | 1603 bp |
| gD | ttcccatacactcacctgccagc tcgacgccggtactgcggag | 1250 bp |

Example 3

Pathogenicity Test of the Virus 3.1 Pathogenicity of the Virus in Piglets at Different Days of Age 6 piglets at 34~35 days of age which were negative for pseudorabies antibodies were randomly divided into 2 groups, one with 4 piglets (experimental group) and the other with 2 piglets (control group), wherein the experimental group was inoculated with PRV HN1201 strain by intranasal instillation (challenge dosage is $2 \times 10^{8.0} TCID_{50}$/piglet) and the control group was inoculated with DMEM medium. Meanwhile 4 piglets at 49 days of age were inoculated with third passage of the virulent HN1201 strain after preservation (challenge dose was $2 \times 10^{8.0} TCID_{50}$/piglet), and the control is still piglets at 35 days of age. After inoculation of virus, the temperature of piglets was determined daily, and clinical signs and death status were observed. The results are shown in Table 2.

TABLE 2

Pathogenicity of PRV HN1201 strain in piglets at different days of age

| Group | Number | Days | Inoculation Dose | Clinical signs | Death status |
|---|---|---|---|---|---|
| 1 | A1 | 35 | $2 \times 10^{8.0} TCID_{50}$/piglet | Body Temperature increased, depression, loss of appetite, onset of respiratory and/or neurological signs | Died on day 4 after viral challenge |
|   | A2 |   |   |   | Died on day 5 after viral challenge |
|   | A3 |   |   |   | Died on day 5 after viral challenge |
|   | A4 |   |   |   | Died on day 6 after viral challenge |
| 2 | B1 | 49 | $2 \times 10^{8.0} TCID_{50}$/piglet | Body Temperature increased, depression, loss of appetite, onset of respiratory and/or neurological signs | Died on day 7 after viral challenge |
|   | B2 |   |   |   | Died on day 7 after viral challenge |
|   | B3 |   |   |   | Died on day 5 after viral challenge |
|   | B4 |   |   |   | Survived |
| 3 | C1 | 35 | DMEM control | Normal | Survived |
|   | C2 |   |   |   | Survived |

It showed in the results that inoculation with PRV HN1201 strain in piglets at different days of age could lead to onset of pseudorabies in piglets, as well as death of over ¾ of inoculated piglets.

3.2 Pathogenicity of the Virus at Different Doses in Piglets 8 piglets at 49 days of age which were negative for pseudorabies antibodies were randomly divided into 2 groups, each with 4 piglets, in addition two more piglets were used as control. The experimental groups were inoculated with $2 \times 10^{7.0} TCID_{50}$/piglet PRV HN1201 strain or $2 \times 10^{8.0} TCID_{50}$/piglet PRV HN1201 strain by intranasal instillation, respectively, and the control group was inoculated with DMEM medium. After inoculation of virus, the body temperature of piglets was determined daily, and clinical signs and death status were observed. The results are shown in Table 3.

TABLE 3

Pathogenicity of different doses of PRV HN1201 strain in piglets

| Group | Number | Inoculation Dose | Clinical signs | Death status |
|---|---|---|---|---|
| 1 | A1 | $2 \times 10^{7.0} TCID_{50}$/piglet | Significant clinical signs: temperature increased, depression, loss of appetite | Died on day 5 after viral challenge |
|   | A2 |   |   | Died on day 6 after viral challenge |
|   | A3 |   |   | Died on day 6 after viral challenge |
|   | A4 |   |   | Died on day 6 after viral challenge |
| 2 | B1 | $2 \times 10^{8.0} TCID_{50}$/piglet | Significant clinical signs: temperature increased, depression, loss of appetite | Died on day 2 after viral challenge |
|   | B2 |   |   | Died on day 3 after viral challenge |
|   | B3 |   |   | Died on day 4 after viral challenge |
|   | B4 |   |   | Died on day 4 after viral challenge |
| 3 | C1 |   | DMEM control | Normal | Survived |
|   | C2 |   |   | Survived |

It showed in the results that inoculation with different doses of clinically isolated PRV HN1201 strain in piglets at 49 days of age could all lead to onset of pseudorabies in piglets, of which 4/4 died.

Example 4

Preparation of the Inactivated PRV Vaccine

The culture of different passages of the isolated strain was inoculated, according to Table 4, onto PK-15 cell culture to form a seed lot which was then inoculated into a monolayer of PK cell culture at 1% (V/V) of the amount of the liquid virus medium, and placed in a rotary incubator at 37° C. The cell medium containing viruses was harvested when the cytopathic effect of cells reached to 80%; the viruses were harvested after 2 times of freezing-thawing and the virus titer was assessed. 10% (V/V) formaldehyde solution was added to different passages of virus solution respectively, with a final concentration of 0.2% (V/V). The virus solution was inactivated at 37° C. for 18 hours, being stirred for 10 min every 4 hours, and diluted with pH 7.4 phosphate-buffered saline (PBS) to the content of viruses as shown in Table 4, mixed with 206 adjuvant (SEPPIC, France) according to the volume ratio of 54:46, and stirred at 120 rpm for 15 min at 30° C.

TABLE 4

Preparation of each group of pseudorabies vaccines

| Group | Passage number of HN1201 culture | Content of virus before inactivation | Ratio of vaccines (inactivated virus solution:206 adjuvant) |
|---|---|---|---|
| A | 5 | $10^{8.43} TCID_{50}$/mL | 54:46 |
| B | 35 | $10^{6.0} TCID_{50}$/mL | 54:46 |

Example 5

Immunogenicity Assay of Inactivated Vaccines 16 piglets at 21 days of age which were negative for PRV antibodies were randomly divided into 4 groups, each with 4 piglets, and injected with vaccines according to Table 5. Two groups injected with inactivated vaccines were injected with 2 ml/piglet of the inactivated vaccines against pseudorabies prepared in Example 4. As a control vaccine, the live vaccine SA215 strain prepared by using the method in CN101186902 was applied according to the method for determining immunogenicity in the specification of the patent. The control group was inoculated with 2 mL/piglet of DMEM medium.

TABLE 5

Grouping of immunogenicity assay

| Group | Vaccines injected | Dose |
|---|---|---|
| Group A injected with inactivated vaccine | Group A vaccine prepared in Example 4 | 2 mL/piglet |
| Group B injected with inactivated vaccine | Group B vaccine prepared in Example 4 | 2 mL/piglet |
| Group injected with Live vaccine SA215 | Live PRV vaccine | $10^{6.0}TCID_{50}$/piglet |
| Control group | DMEM medium | 2 mL/piglet |

After immunization with vaccines, neutralizing titers of antibodies of the inactivated vaccines groups were determined weekly according to the method of serum neutralization test from GB/T18641-2002 Diagnostic Techniques for Aujeszk's Disease. The results are shown in Table 6.

TABLE 6

Nneutralizing titers of antibodies at different time in piglets after immunization with PRV inactivated vaccines

| | Average value of neutralizing titers of antibodies at different time (weeks) | | | |
|---|---|---|---|---|
| Group | 1 | 2 | 3 | 4 |
| Group A injected with inactivated vaccine | 1:4.8 | 1:11.2 | 1:16.0 | 1:37.7 |
| Group B injected with inactivated vaccine | 1:4.0 | 1:6.3 | 1:13.5 | 1:22.4 |
| Group injected with live vaccine | 1:3.7 | 1:4.0 | 1:10.0 | 1:16.0 |
| Control group | Negative | Negative | Negative | Negative |

The result from Table 6 indicated that immunization with inactivated PRV vaccines in piglets can produce high neutralizing titers which increase with immunization time.

The piglets were challenged with $2 \times 10^{8.0}TCID_{50}$/piglet of PRV HN1201 strain on day 28 after immunization, clinical signs and death status were observed as shown in Table 7. After challenge the body temperature of piglets was determined daily as shown in Table 8.

TABLE 7

Viral challenge for piglets after immunization with PRV inactivated vaccines

| Group | clinical signs and death status | Rate of protection |
|---|---|---|
| Group A injected with inactivated vaccine | Body temperature increased for 2-3 days, normal appetite, basically no neurological signs, survived | 100% (4/4) |
| Group B injected with inactivated vaccine | Body temperature increased for 2-3 days, normal appetite, basically no neurological signs, survived | 100% (4/4) |
| Group injected with live vaccine | Body temperature increased for 7-10 days, loss of appetite, significant neurological signs, survived | 100% (4/4) |
| Control group | Significant signs, two piglets died on day 2 after challenge, and all died within 3 days after challenge. | 0% (0/4) |

TABLE 8

Body temperature change after challenge for piglets immunized with PRV vaccines

| Day | Group A injected with inactivated vaccine | Group B injected with inactivated vaccine | Group injected with live vaccine |
|---|---|---|---|
| day 1 after challenge | 39.5 | 39.6 | 39.4 |
| day 2 after challenge | 41.2 | 41.6 | 41.8 |
| day 3 after challenge | 40.5 | 40.3 | 41.2 |
| day 4 after challenge | 40.2 | 39.7 | 41.6 |
| day 5 after challenge | 39.7 | 39.5 | 41.4 |
| day 6 after challenge | 39.6 | 39.4 | 41.3 |
| day 7 after challenge | 39.7 | 39.5 | 41.4 |
| day 8 after challenge | 39.5 | 39.7 | 41.2 |
| day 9 after challenge | 39.6 | 39.4 | 41.5 |
| day 10 after challenge | 39.2 | 39.5 | 40.6 |
| day 11 after challenge | 39.5 | 39.7 | 39.7 |
| day 12 after challenge | 39.4 | 39.5 | 39.8 |
| day 13 after challenge | 39.3 | 39.4 | 39.7 |
| day 14 after challenge | 39.2 | 39.1 | 39.4 |

The results from Table 7 and 8 indicated that immunization of piglets with inactivated PRV vaccines could provide a 100% (4/4) protection rate for piglets, even though the infection of viruses could not be avoided (they showed clinical signs), while all piglets in the control group died on day 4 after challenge, therefore the inactivated PRV vaccines can provide excellent protection. In addition, compared with the live vaccine as the control vaccine, it took less time for the body temperature of piglets immunized with the inactivated vaccines to increase, and also they kept a basically normal appetite with no clinical signs, indicating excellent immune protection.

Example 6

Preparation of the PRV gD Protein

1. Amplification of the PRV gD Gene

The PK-15 cells which were in excellent health were inoculated with the PRV HN1201 strain or culture thereof of different passages (the PRV strain was HN1201 strain (Pseudorabies virus, strain HN1201), of which the accession number was CCTCC NO. V 201311; the HN1201 strain was deposited in the China Center for Type Culture Collection (CCTCC) on May, 20, 2013, of which the address was Wuhan University, Wuhan City, Hubei Province), the culture of different passages was the culture within 5~35 passages. The PRV genomic DNA was extracted by using MiniBEST Viral RNA/DNA Extraction Kit Ver.3.0 (TAKARA) after harvesting viruses. PCR amplification was performed by using 1 μL genomic DNA as template and gD-specific primers:

```
gDSF: 5' ATGCTGCTCGCAGCGCTATTGGC 3'
and gDSR: 5' CTACGGACCGGGCTGCGCTTTTAG3'.
```

The high fidelity polymerase, Prime STAR® HS DNA Polymerase with GC Buffer (TAKARA) was used in the PCR reaction. The amplification conditions were: 94° C. 3 min; 94° C. 30 s, 68° C. 90 s, 30 cycles; 72° C. 5 min. The PCR product was named gD, of which the nucleotide sequence is shown in SEQ No.4, and the amino acid sequence can be derived as shown in SEQ No.1.

2. Acquisition and Identification of Recombinant Bacmid

The PCR product, gD obtained from amplification with the high fidelity polymerase was cloned into the pFastBac/HBM-TOPO vector (Invitrogen, A11339). The cloning system was as follows: 4 μL PCR product, gD, 1 μL salt solution, 1 μL TOPO vector; 6 μL in total. The mixture was mixed thoroughly and incubated at room temperature for 5 minutes, and then used to transform One Shot® Mach1™ T1R competent cells. The transformation mix was spread onto plates containing ampicillin. A single colony was picked to identify insert directionality of gD gene, and the plasmid with the correct insert directionality was delivered to Invitrogen for sequencing, in order to verify the correct sequence. The plasmid with the correct sequence was named pFastBac/HBM-TOPO-gD.

After the pFastBac/HBM-TOPO-gD plasmid was transformed into DH10Bac competent cells, transposition occurred between the pFastBac/HBM-TOPO-gD plasmid and the shuttle plasmid Bacmid in the competent cells, and the resulting recombinant plasmid was extracted by using PureLink™ HiPure Plasmid DNA Miniprep Kit (Invitrogen), and the insertion of gD was identified with pUCM13 Forward/pUCM13 Reverse primer. The positive Bacmid was named Bacmid-gD.

3. Transfection for Obtaining Recombinant Baculovirus

This step was carried out based on the method provided by the instruction of Bac-to-Bac HBM TOPO Secreted Expression System (Invitrogen). $8 \times 10^5$ sf9 cells were layered in each well of a 6-well plate, transfection was performed according to the instruction of Cellfectin® II transfection agent after adherence of the cells: 8 μL Cellfectin® II and 1 μg Bacmid-gD DNA were diluted respectively with 100 μL SF-900 II medium and mixed by vortex. The diluted DNA was combined with the diluted Cellfectin® II (total volume ~210 μL), mixed thoroughly and incubated for 15-30 minutes at room temperature. The transfection mixture was then added dropwise onto the cells. The supernatant of cell culture, marked as P0 recombinant baculovirus vBac-gD, was collected 72 h after transfection or until the cytopathic effect was visible. The P0 recombinant baculovirus vBac-gD infected sf9 cells, and after three rounds of amplification the resulting P3 recombinant baculovirus vBac-gD was used for expressing the recombinant protein.

4. Infection of High-Five Cells with the Recombinant Baculovirus for Expression of the Recombinant Protein The P3 recombinant baculovirus vBac-gD was inoculated in High-five cells (Invitrogen, B85502). Suspension culture of High-five cells was performed in a 500 mL Erlenmeyer flask and the cells were inoculated with the virus with an MOI of 1 when the cell density reached to $7.0 \times 10^5$ cell/mL. The supernatant of cell culture was collected 72 h after infection. A Tangential Flow Filtration System (Millipore) was employed to concentrate the volume into 1/10 of the original one. 1% (V %) of Triton X-100 (Sigma) was used to inactivate the baculovirus, and the content of protein determined by SD S-PAGE optical density method was 200 μg/mL.

Example 7

Preparation of the PRV Subunit Vaccines

The subunit antigens prepared in Example 6 were diluted with PBS (pH=7.4) to the contents of protein in Table 9, mixed with 206 adjuvant (SEPPIC, France) at a volume ratio of 54:46, and stirred at 120 rpm for 15 min at 30° C.

TABLE 9

Preparation of each group of the pseudorabies subunit vaccines

| Group | Content of protein | Ratio of vaccines (inactivated virus solution:206 adjuvant) |
|---|---|---|
| A | 25 μg/mL | 54:46 |
| B | 100 μg/mL | 54:46 |

Example 8

Immunogenicity Assay of the Vaccines in Pigs 12 piglets at 21 days of age which were negative for PRV antibodies were randomly divided into 3 groups, each with 4 piglets, and injected with 2 ml/piglet of the subunit vaccines against PRV prepared in Example 7 according to Table 10. The control group was inoculated with 2 mL/piglet of DMEM medium.

TABLE 10

Grouping of immunogenicity assay

| Group | Vaccines injected | Dose |
|---|---|---|
| Group A injected with subunit vaccine | Group A vaccine prepared in Example 7 | 2 mL/piglet |
| Group B injected with subunit vaccine | Group B vaccine prepared in Example 7 | 2 mL/piglet |
| Control group | DMEM medium | 2 mL/piglet |

The piglets were challenged with $2\times10^{8.0}TCID_{50}$/piglet of PRV HN1201 strain on day 28 after immunization, and clinical signs and death status were observed as shown in Table 11. After challenge the body temperature of piglets was determined daily as shown in Table 12.

TABLE 11

Viral challenge for piglets after immunization with the PRV subunit vaccines

| Group | Clinical signs and death status | Rate of protection |
|---|---|---|
| Group A injected with subunit vaccine | Body temperature increased for 2-3 days, normal appetite, basically no neurological signs, survived | 100% (4/4) |
| Group B injected with subunit vaccine | Body temperature increased for 2-3 days, normal appetite, basically no neurological signs, survived | 100% (4/4) |
| Control group | Significant signs, two died on day 2 after challenge, and all died within 3 days after challenge. | 0% (0/4) |

TABLE 12

Body temperature change of piglets immunized with the PRV subunit vaccines after challenge

| Day | Group A injected with subunit vaccine | Group B injected with subunit vaccine |
|---|---|---|
| day 1 after challenge | 39.5 | 39.5 |
| day 2 after challenge | 41.2 | 41.6 |
| day 3 after challenge | 40.3 | 40.2 |
| day 4 after challenge | 40.1 | 39.7 |
| day 5 after challenge | 39.6 | 39.5 |
| day 6 after challenge | 39.6 | 39.3 |

TABLE 12-continued

Body temperature change of piglets immunized
with the PRV subunit vaccines after challenge

| Day | Group A injected with subunit vaccine | Group B injected with subunit vaccine |
|---|---|---|
| day 7 after challenge | 39.6 | 39.5 |
| day 8 after challenge | 39.5 | 39.4 |
| day 9 after challenge | 39.5 | 39.6 |
| day 10 after challenge | 39.2 | 39.3 |
| day 11 after challenge | 39.3 | 39.4 |
| day 12 after challenge | 39.4 | 39.4 |
| day 13 after challenge | 39.2 | 39.4 |
| day 14 after challenge | 39.2 | 39.1 |

The results from Table 11 and 12 indicated that immunization with the PRV subunit vaccines for piglets could provide a 100% (4/4) protection rate for piglets, even though the infection of viruses could not be avoided (they showed clinical signs), while all the control piglets died on day 4 after challenge, therefore the PRV subunit vaccines can provide excellent protection.

Those are only preferred embodiments of the present invention as described above, which cannot be used to limit the present invention. Any change, substitution or modification etc., which are within the spirit and principle of the invention, should be included within the scope of protection of the present invention.

What is claimed is:

1. A vaccine composition, comprising an immunogenic amount of inactivated vaccine of a porcine pseudorabies virus strain comprising gD glycoprotein encoded by the nucleotide sequence as shown in SEQ ID NO: 4, gB glycoprotein encoded by the nucleotide sequence as shown in SEQ ID NO: 5, wherein said pseudorabies virus strain is the HN1201 strain or culture thereof, of which the accession number is China Center for Type Culture Collection (CCTCC) NO. V 201311; said vaccine composition further comprising medium, adjuvants and excipient.

2. The vaccine composition as described in claim 1, wherein said vaccine composition comprises an inactivated vaccine of the PRV HN1201 strain of culture thereof, of which the concentration is not less than $10^{6.0} TCID_{50}/mL$.

3. The vaccine composition as described in claim 1, wherein said vaccine composition comprises between 25 and 100 μg/dose gD protein antigen of the PRV HN1201 strain or culture thereof.

* * * * *

SEQUENCE LISTING

<160> NUMBER OF SEQ ID NOS: 6

<210> SEQ ID NO 1
<211> LENGTH: 402
<212> TYPE: PRT
<213> ORGANISM: pseudorabies virus

<400> SEQUENCE: 1

Met Leu Leu Ala Ala Leu Leu Ala Ala Leu Val Ala Arg Thr Thr Leu
1 5 10 15

Gly Ala Asp Val Asp Ala Val Pro Ala Pro Thr Phe Pro Pro Pro Ala
20 25 30

Tyr Pro Tyr Thr Glu Ser Trp Gln Leu Thr Leu Thr Thr Val Pro Ser
35 40 45

Pro Phe Val Gly Pro Ala Asp Val Tyr His Thr Arg Pro Leu Glu Asp
50 55 60

Pro Cys Gly Val Val Ala Leu Ile Ser Asp Pro Gln Val Asp Arg Leu
65 70 75 80

Leu Asn Glu Ala Val Ala His Arg Arg Pro Thr Tyr Arg Ala His Val
85 90 95

Ala Trp Tyr Arg Ile Ala Asp Gly Cys Ala His Leu Leu Tyr Phe Ile
100 105 110

Glu Tyr Ala Asp Cys Asp Pro Arg Gln Ile Phe Gly Arg Cys Arg Arg
115 120 125

Arg Thr Thr Pro Met Trp Trp Thr Pro Ser Ala Asp Tyr Met Phe Pro
130 135 140

Thr Glu Asp Glu Leu Gly Leu Leu Met Val Ala Pro Gly Arg Phe Asn
145 150 155 160

Glu Gly Gln Tyr Arg Arg Leu Val Ser Val Asp Gly Val Asn Ile Leu
165 170 175

Thr Asp Phe Met Val Ala Leu Pro Glu Gly Gln Glu Cys Pro Phe Ala
180 185 190

Arg Val Asp Gln His Arg Thr Tyr Lys Phe Gly Ala Cys Trp Ser Asp
195 200 205

Asp Ser Phe Lys Arg Gly Val Asp Val Met Arg Phe Leu Thr Pro Phe
210 215 220

Tyr Gln Gln Pro Pro His Arg Glu Val Val Asn Tyr Trp Tyr Arg Lys
225 230 235 240

Asn Gly Arg Thr Leu Pro Arg Ala Tyr Ala Ala Ala Thr Pro Tyr Ala
245 250 255

Ile Asp Pro Ala Arg Pro Ser Ala Gly Ser Pro Arg Pro Arg Pro Arg

```
                    260                 265                 270
Pro Arg Pro Arg Pro Arg Pro Lys Pro Glu Pro Ala Pro Ala Thr Pro
                275                 280                 285
Ala Pro Pro Gly Arg Leu Pro Glu Pro Ala Thr Arg Asp His Ala Ala
            290                 295                 300
Gly Gly Arg Pro Thr Pro Arg Pro Pro Arg Pro Glu Thr Pro His Arg
305                 310                 315                 320
Pro Phe Ala Pro Ala Val Val Pro Ser Gly Trp Pro Gln Pro Ala
                325                 330                 335
Glu Pro Phe Pro Pro Arg Thr Thr Ala Ala Pro Gly Val Ser Arg His
                340                 345                 350
Arg Ser Val Ile Val Gly Thr Gly Thr Ala Met Gly Ala Leu Leu Val
            355                 360                 365
Gly Val Cys Val Tyr Ile Phe Phe Arg Leu Arg Gly Ala Lys Gly Tyr
            370                 375                 380
Arg Leu Leu Gly Gly Pro Ala Asp Ala Asp Glu Leu Lys Ala Gln Pro
385                 390                 395                 400
Gly Pro

<210> SEQ ID NO 2
<211> LENGTH: 914
<212> TYPE: PRT
<213> ORGANISM: pseudorabies virus

<400> SEQUENCE: 2

Met Pro Ala Gly Gly Gly Leu Trp Arg Gly Pro Arg Gly His Arg Pro
1               5                   10                  15
Gly His His Gly Gly Ala Gly Leu Gly Arg Leu Trp Pro Ala Pro His
            20                  25                  30
His Ala Ala Ala Arg Gly Ala Val Ala Leu Ala Leu Leu Leu Leu
        35                  40                  45
Ala Leu Ala Ala Thr Pro Thr Cys Gly Ala Ala Ala Val Thr Arg Ala
    50                  55                  60
Ala Ser Ala Ser Pro Ala Pro Gly Thr Gly Ala Thr Pro Asp Gly Phe
65                  70                  75                  80
Ser Ala Glu Glu Ser Leu Glu Glu Ile Asp Gly Ala Val Ser Pro Gly
                85                  90                  95
Pro Ser Asp Ala Pro Asp Gly Glu Tyr Gly Asp Leu Asp Ala Arg Thr
            100                 105                 110
Ala Val Arg Ala Ala Thr Glu Arg Asp Arg Phe Tyr Val Cys Pro
            115                 120                 125
Pro Pro Ser Gly Ser Thr Val Val Arg Leu Glu Pro Glu Gln Ala Cys
        130                 135                 140
Pro Glu Tyr Ser Gln Gly Arg Asn Phe Thr Glu Gly Ile Ala Val Leu
145                 150                 155                 160
Phe Lys Glu Asn Ile Ala Pro His Lys Phe Lys Ala His Ile Tyr Tyr
                165                 170                 175
Lys Asn Val Ile Val Thr Thr Val Trp Ser Gly Ser Thr Tyr Ala Ala
            180                 185                 190
Ile Thr Asn Arg Phe Thr Asp Arg Val Pro Val Pro Val Gln Glu Ile
            195                 200                 205
Thr Asp Val Ile Asp Arg Arg Gly Lys Cys Val Ser Lys Ala Glu Tyr
        210                 215                 220
Val Arg Asn Asn His Lys Val Thr Ala Phe Asp Arg Asp Glu Asn Pro
```

```
             225                 230                 235                 240
Val Glu Val Asp Leu Arg Pro Ser Arg Leu Asn Ala Leu Gly Thr Arg
                    245                 250                 255

Gly Trp His Thr Thr Asn Asp Thr Tyr Thr Lys Ile Gly Ala Ala Gly
                    260                 265                 270

Phe Tyr His Thr Gly Thr Ser Val Asn Cys Ile Val Glu Glu Val Glu
                    275                 280                 285

Ala Arg Ser Val Tyr Pro Tyr Asp Ser Phe Ala Leu Ser Thr Gly Asp
                    290                 295                 300

Ile Val Tyr Met Ser Pro Phe Tyr Gly Leu Arg Glu Gly Ala His Gly
305                 310                 315                 320

Glu His Ile Gly Tyr Ala Pro Gly Arg Phe Gln Gln Val Glu His Tyr
                    325                 330                 335

Tyr Pro Ile Asp Leu Asp Ser Arg Leu Arg Ala Ser Glu Ser Val Thr
                    340                 345                 350

Arg Asn Phe Leu Arg Thr Pro His Phe Thr Val Ala Trp Asp Trp Ala
                    355                 360                 365

Pro Lys Thr Arg Arg Val Cys Ser Leu Ala Lys Trp Arg Glu Ala Glu
                    370                 375                 380

Glu Met Ile Arg Asp Glu Thr Arg Asp Gly Ser Phe Arg Phe Thr Ser
385                 390                 395                 400

Arg Ala Leu Gly Ala Ser Phe Val Ser Asp Val Thr Gln Leu Asp Leu
                    405                 410                 415

Gln Arg Val His Leu Gly Asp Cys Val Leu Arg Glu Ala Ser Glu Ala
                    420                 425                 430

Ile Asp Ala Ile Tyr Arg Arg Tyr Asn Asn Thr His Val Leu Ala
                    435                 440                 445

Gly Asp Lys Pro Glu Val Tyr Leu Ala Arg Gly Gly Phe Val Val Ala
                    450                 455                 460

Phe Arg Pro Leu Ile Ser Asn Glu Leu Ala Gln Leu Tyr Ala Arg Glu
465                 470                 475                 480

Leu Glu Arg Leu Gly Leu Ala Gly Val Val Gly Pro Ala Ser Pro Ala
                    485                 490                 495

Ala Ala Arg Arg Ala Arg Arg Ser Pro Gly Pro Ala Gly Thr Pro Glu
                    500                 505                 510

Pro Pro Ala Val Asn Gly Thr Gly His Leu Arg Ile Thr Thr Gly Ser
                    515                 520                 525

Ala Glu Phe Ala Arg Leu Gln Phe Thr Tyr Asp His Ile Gln Ala His
                    530                 535                 540

Val Asn Asp Met Leu Ser Arg Ile Ala Ala Trp Cys Glu Leu Gln
545                 550                 555                 560

Asn Lys Asp Arg Thr Leu Trp Gly Glu Met Ser Arg Leu Asn Pro Ser
                    565                 570                 575

Ala Val Ala Thr Ala Ala Leu Gly Gln Arg Val Ser Ala Arg Met Leu
                    580                 585                 590

Gly Asp Val Met Ala Ile Ser Arg Cys Val Glu Val Arg Gly Gly Val
                    595                 600                 605

Tyr Val Gln Asn Ser Met Arg Val Pro Gly Glu Arg Gly Thr Cys Tyr
                    610                 615                 620

Ser Arg Pro Leu Val Thr Phe Glu His Asn Gly Thr Gly Val Ile Glu
625                 630                 635                 640

Gly Gln Leu Gly Asp Asp Asn Glu Leu Leu Ile Ser Arg Asp Leu Ile
                    645                 650                 655
```

Glu Pro Cys Thr Gly Asn His Arg Arg Tyr Phe Lys Leu Gly Gly Gly
            660                 665                 670

Tyr Val Tyr Tyr Glu Asp Tyr Ser Tyr Val Arg Met Val Glu Val Pro
        675                 680                 685

Glu Thr Ile Ser Thr Arg Val Thr Leu Asn Leu Thr Leu Leu Glu Asp
690                 695                 700

Arg Glu Phe Leu Pro Leu Glu Val Tyr Thr Arg Glu Glu Leu Ala Asp
705                 710                 715                 720

Thr Gly Leu Leu Asp Tyr Ser Glu Ile Gln Arg Arg Asn Gln Leu His
                725                 730                 735

Ala Leu Lys Phe Tyr Asp Ile Asp Arg Val Val Lys Val Asp His Asn
            740                 745                 750

Val Val Leu Leu Arg Gly Ile Ala Asn Phe Phe Gln Gly Leu Gly Asp
        755                 760                 765

Val Gly Ala Ala Val Gly Lys Val Val Leu Gly Ala Thr Gly Ala Val
    770                 775                 780

Ile Ser Ala Val Gly Gly Met Val Ser Phe Leu Ser Asn Pro Phe Gly
785                 790                 795                 800

Ala Leu Ala Ile Gly Leu Leu Val Leu Ala Gly Leu Val Ala Ala Phe
                805                 810                 815

Leu Ala Tyr Arg His Ile Ser Arg Leu Arg Arg Asn Pro Met Lys Ala
            820                 825                 830

Leu Tyr Pro Val Thr Thr Lys Ala Leu Lys Glu Asp Gly Val Glu Glu
        835                 840                 845

Asp Asp Val Asp Glu Ala Lys Leu Asp Gln Ala Arg Asp Met Ile Arg
    850                 855                 860

Tyr Met Ser Ile Val Ser Ala Leu Glu Gln Gln Glu His Lys Ala Arg
865                 870                 875                 880

Lys Lys Asn Ser Gly Pro Ala Leu Leu Ala Ser Arg Val Gly Ala Met
                885                 890                 895

Ala Thr Arg Arg Arg His Tyr Gln Arg Leu Glu Asn Glu Asp Pro Asp
            900                 905                 910

Ala Pro

<210> SEQ ID NO 3
<211> LENGTH: 487
<212> TYPE: PRT
<213> ORGANISM: pseudorabies virus

<400> SEQUENCE: 3

Met Ala Ser Leu Ala Arg Ala Met Leu Ala Leu Leu Ala Leu Tyr Thr
1               5                   10                  15

Ala Ala Ile Ala Ala Ala Pro Ser Ser Thr Thr Ala Leu Gly Thr Thr
            20                  25                  30

Pro Asn Gly Gly Gly Gly Asn Ser Ser Ala Gly Glu Leu Ser Pro
        35                  40                  45

Ser Pro Pro Ser Thr Pro Glu Pro Val Ser Gly Thr Thr Gly Ala Ala
    50                  55                  60

Ala Ser Thr Pro Ala Ala Val Ser Thr Pro Arg Val Pro Pro Ser
65                  70                  75                  80

Val Ser Arg Arg Lys Pro Gln Arg Asn Gly Asn Arg Thr Arg Val His
                85                  90                  95

Gly Asp Lys Ala Thr Ser His Gly Arg Lys Arg Ile Val Cys Arg Glu
            100                 105                 110

Arg Leu Phe Ser Ala Arg Val Gly Asp Ala Val Ser Phe Gly Cys Ala
            115                 120                 125

Val Val Pro Arg Ala Gly Glu Thr Phe Glu Val Arg Phe Cys Arg Arg
        130                 135                 140

Gly Arg Phe Arg Ser Pro Asp Ala Asp Pro Glu Tyr Phe Asp Glu Pro
145                 150                 155                 160

Pro Arg Pro Glu Leu Pro Arg Glu Arg Leu Leu Phe Ser Ser Ala Asn
                165                 170                 175

Ala Ser Leu Ala His Ala Asp Ala Leu Ala Ser Ala Val Val Val Glu
            180                 185                 190

Gly Glu Arg Ala Thr Val Ala Asn Val Ser Gly Glu Val Ser Val Arg
        195                 200                 205

Val Ala Ala Ala Asp Ala Glu Thr Glu Gly Val Tyr Thr Trp Arg Val
    210                 215                 220

Leu Ser Ala Asn Gly Thr Glu Val Arg Ser Ala Asn Val Ser Leu Val
225                 230                 235                 240

Leu Tyr Ser Gln Pro Glu Phe Gly Leu Ser Ala Pro Val Leu Phe
                245                 250                 255

Gly Glu Pro Phe Arg Ala Val Cys Val Val Arg Asp Tyr Tyr Pro Arg
            260                 265                 270

Arg Ser Val Arg Leu Arg Trp Phe Ala Asp Glu His Pro Val Asp Ala
        275                 280                 285

Ala Phe Val Thr Asn Ser Thr Val Ala Asp Glu Leu Gly Arg Arg Thr
    290                 295                 300

Arg Val Ser Val Val Asn Val Thr Arg Ala Asp Val Pro Gly Leu Ala
305                 310                 315                 320

Ala Ala Asp Asp Ala Asp Ala Leu Ala Pro Ser Leu Arg Cys Glu Ala
                325                 330                 335

Val Trp Tyr Arg Asp Ser Val Ala Ser Gln Arg Phe Ser Glu Ala Leu
            340                 345                 350

Arg Pro His Val Tyr His Pro Ala Ala Val Ser Val Arg Phe Val Glu
        355                 360                 365

Gly Phe Ala Val Cys Asp Gly Leu Cys Val Pro Glu Ala Arg Leu
    370                 375                 380

Ala Trp Ser Asp His Ala Ala Asp Thr Val Tyr His Leu Gly Ala Cys
385                 390                 395                 400

Ala Glu His Pro Gly Leu Leu Asn Val Arg Ser Ala Arg Pro Leu Ser
                405                 410                 415

Asp Leu Asp Gly Pro Val Asp Tyr Thr Cys Arg Leu Glu Gly Met Pro
            420                 425                 430

Ser Gln Leu Pro Ile Phe Glu Asp Thr Gln Arg Tyr Asp Ala Ser Pro
        435                 440                 445

Thr Ser Val Ser Trp Pro Val Val Thr Ser Met Ile Thr Val Ile Ala
    450                 455                 460

Gly Ile Ala Ile Leu Ala Ile Val Leu Val Ile Met Ala Thr Cys Val
465                 470                 475                 480

Tyr Tyr Arg Arg Ala Gly Pro
                485

<210> SEQ ID NO 4
<211> LENGTH: 1209
<212> TYPE: DNA
<213> ORGANISM: pseudorabies virus

<400> SEQUENCE: 4

```
atgctgctcg cagcgctatt ggcggcgctg gtcgcccgga cgacgctcgg cgcggacgtg      60
gacgccgtgc ccgcgccgac cttcccccg cccgcgtacc cgtacaccga gtcgtggcag     120
ctgacgctga cgacggtccc ctcgcccttc gtcggcccg cggacgtcta ccacacgcgc     180
ccgctggagg acccgtgcgg ggtggtggcg ctgatctccg acccgcaggt ggaccggctg     240
ctgaacgagg cggtggccca ccggcggccc acgtaccgcg cccacgtggc ctggtaccgc     300
atcgcggacg ggtgcgcgca cctgctgtac tttatcgagt acgccgactg cgaccccagg     360
cagatctttg ggcgctgccg cgccgcacc acgccgatgt ggtggacccc gtccgcggac     420
tacatgttcc ccacggagga cgagctgggg ctgctcatgg tggccccggg gcggttcaac     480
gagggccagt accggcgcct ggtgtccgtc gacggcgtga acatcctcac cgacttcatg     540
gtggcgctcc ccgaggggca agagtgcccg ttcgcccgcg tggaccagca ccgcacgtac     600
aagttcggcg cgtgctggag cgacgacagc ttcaagcggg gcgtggacgt gatgcgattc     660
ctgacgccgt tctaccagca gccccgcac cgggaggtgg tgaactactg gtaccgcaag     720
aacggccgga cgctcccgcg ggcctacgcc gccgcacgc cgtacgccat cgaccccgcg     780
cggccctcgg cgggctcgcc gaggcccagg ccccggcccc ggcccaggcc ccggccgaag     840
cccgagcccg ccccggcgac gccgcgcgcc ccggccgcc tgcccgagcc ggcgacgcgg     900
gaccacgccg ccggggggcg ccccacgcgc cgaccccccga ggcccgagac gccgcaccgc     960
cccttcgccc cgccggccgt cgtgcccagc gggtggccgc agcccgcgga gccgttcccg    1020
ccccggacca ccgccgcgcc gggcgtctcg cgccaccgct cggtgatcgt cggcacgggc    1080
accgcgatgg gcgcgctcct ggtgggcgtg tgcgtctaca tcttcttccg cctgagggg    1140
gcgaaggggt atcgcctcct gggcggtccc gcggacgccg acgagctaaa agcgcagccc    1200
ggtccgtag                                                            1209
```

<210> SEQ ID NO 5
<211> LENGTH: 2745
<212> TYPE: DNA
<213> ORGANISM: pseudorabies virus

<400> SEQUENCE: 5

```
ctaggggcg tcggggtcct cgttctcgag gcgctggtag tgccggcggc gcgtggccat      60
cgccccgacg cggctggcca gcagcgcggg cccgctgttc ttcttgcgcg ccttgtgctc     120
ctgctgctcg agggccgaca cgatggacat gtaccggatc atgtcccggg cctggtccag     180
cttggcctcg tccacgtcgt cctcttcgac gccgtcctcc ttgagcgcct tcgtcgtgac     240
ggggtacagg gccttcatgg ggttgcggcg caggcgcgag atgtgccggt aggccaggaa     300
ggccgcgacc aggccggcca gcaccagcag cccgatggcg agcgccccga agggggttgga     360
caggaaggac accatgccgc cgacggccga gatcacggcc ccgtggcgc ccaggaccac     420
cttgccgacg gcgcgcccca cgtcgccgag gccctggaag aagttggcga tgccgcgcag     480
cagcaccacg ttgtggtcca ccttgaccac gcggtcaatg tcgtagaact tgagcgcgtg     540
cagctggttg cggcgctgga tctcgctgta gtccaggagg cccgtgtcgg cgagctcctc     600
gcgcgtgtac acctcgaggg gcaggaactc gcggtcctcg agcagcgtca ggttcagggt     660
cacccgcgtg ctgatcgtct cgggcacctc caccatgcgc acgtagctgt agtcctcgta     720
gtacacgtac ccgccgccca gcttaaagta gcgccggtgt ttgccggtgc agggctcgat     780
gaggtcgcgc gagatgagga gctcgttgtc gtcgccgagc tggccctcga tcacgcccgt     840
```

```
gccgttgtgc tcgaaggtca ccagcgggcg gctgtagcac gtgccgcgct cgccgggcac      900
gcgcatggag ttctgcacgt acacgccgcc gcgcacctcc acgcaccgcg agatggccat      960
cacgtcgccg agcatgcgcg ccgagacgcg ctggcccagc gcggccgtgg ccacggcgct     1020
ggggttcagg cgcgacatct cgccccacag ggtgcggtcc ttgttctgca gctcgcacca     1080
ggcggccgcg atgcggctca gcatgtcgtt cacgtgcgcc tggatgtggt cgtaggtgaa     1140
ctgcaggcgc gcaaactcgg ccgagcccgt ggtgatgcgc aggtgccccg tgccgttgac     1200
ggccggcggc tcgggcgtcc ccgccgggcc gggggagcgc cgggcccgac gggcggccgc     1260
gggggacgcg gggcccacga cgccggcgag gccgaggcgc tcgagctcgc gcgcgtacag     1320
ctgcgccagc tcgttcgaga tcagcgggcg gaaggccacc acgaagcccc cgcgggcgag     1380
gtacacctcg ggcttgtcgc cggccagcac gtgcgtgttg ttgtagcgcc gccggtagat     1440
ggcgtcgatg cctccgagg cctcgcggag gacgcagtcg cccaggtgca cgcgctgcag     1500
gtcgagctgc gtgacgtcgc tgacgaagga ggcgcccagg gcccgcgacg tgaagcggaa     1560
ggacccgtcg cgcgtctcgt cgcggatcat ctcctcggcc tcgcgccact tggccaggct     1620
gcacacgcgc cgcgtcttgg gggcccagtc ccaggccacc gtgaagtgcg gcgtgcgcag     1680
aaagttgcgc gtcacgctct cggaggcgcg gaggcgcgag tccaggtcga tggggtagta     1740
gtgctccacc tgctggaagc gcccgggcgc gtagccgatg tgctccccgt gggcccctc     1800 gcgcaggccg tagaagggggg acatgtacac gatgtccccc gtggacaggg cgaaggagtc     1860
gtaggggtac acggagcgcg cctccacctc ctcgacgatg cagttgacgg aggtgccgt     1920 gtggtagaag cccgcggcgc cgatcttggt gtaggtgtcg ttggtggtgt gccagccgcg     1980
ggtgccgagc gcgttcaggc gcgaggggcg caggtccacc tcgacggggt tctcgtcgcg     2040
gtcgaaggcg gtcaccttgt ggttgttgcg cacgtactcg gccttggaga cgcacttgcc     2100
gcggcggtcg atcacgtccg tgatctcctg cacggggacg ggcacgcggt ccgtgaagcg     2160
gttcgtgatg gccgcgtacg tgctcccgga ccacacggtc gtgacgatga cgttcttgta     2220
gtagatgtgg gccttgaact tgtgcgggc gatgttctcc ttgaagagca cggcgatccc     2280
ctccgtgaag ttgcgcccct gcgagtactc ggggcaggct gctcgggct ccaggcgcac     2340 caccgtggag ccggacggcg gcgggcagac gtagaagcgg tcccgctcgg tcgcggccgc     2400
gcgcacggcc gtgcgcgcgt ccaggtcgcc gtactcgccg tcggggcgt ccgaggggcc     2460 gggggagacg gccccgtcga tctcctcgag ggactcctcc gcggagaagc cgtctgggt     2520 ggcgcccgtc ccgggcgcgg gcgaggccga ggcggcccgc gtcacggccg ccgcgccgca     2580
cgtcggggtc gcggcgagcg ccagcagcag cagcgctagc gcgacggcgc cccgcgcagc     2640
tgcagcgtgg tgtggagcag gccaaagacg tccgaggcca gcaccgccgt ggtgcccggg     2700
ccgatgcccg cggggcccgc gccaaagacc gccaccagcg ggcat                    2745
```

<210> SEQ ID NO 6
<211> LENGTH: 1464
<212> TYPE: DNA
<213> ORGANISM: pseudorabies virus

<400> SEQUENCE: 6

```
atggcctcgc tcgcgcgtgc gatgctcgcg ctgctggcgc tctacacggc ggccatcgcc       60
gcggcgccgt cgtccacgac ggcgctcggc acgacgccca cgggggcgg ggcggcaac      120 agcagcgcgg gcgagctctc gccctcgccg ccctcgacgc ccgagcccgt ctcggggacg      180
```

```
acggggccg  cggcctccac  gcccgccgcc  gtctcgacgc  cccgggtccc  gccgccctcg   240
gtctcgcgcc  ggaagcccca  gcggaacggc  aacaggacgc  gcgtccacgg  cgacaaggcc   300
acctcgcacg  ggcgcaagcg  catcgtgtgc  cgcgagcggc  tgttctcggc  gagggtgggg   360
gacgcggtca  gcttcgggtg  cgccgtcgtc  ccgcgcgccg  gggagaccct  cgaggtccgc   420
ttctgccgcc  gcgggcgctt  ccgctcgccc  gacgccgacc  ccgagtactt  tgacgagccc   480
ccgcgcccgg  agctcccgcg  ggagcggctc  ctcttcagct  ccgccaacgc  ctccctcgcc   540
cacgcggacg  cgctcgcctc  cgccgtcgtc  gtcgagggcg  agcgcgcgac  cgtcgccaac   600
gtctcgggcg  aggtgtccgt  gcgcgtggcc  gcggcggacg  ccgagaccga  gggcgtctac   660
acgtggcgcg  tgctgtccgc  caacggcacc  gaggtccgca  gcgccaacgt  ctcgctcgtc   720
ctgtacagcc  agcccgagtt  cggcctgagc  gcgccgcccg  tcctcttcgg  cgagcccttc   780
cgggcggtgt  gcgtcgtccg  cgactactac  ccgcggcgca  gcgtgcgcct  gcgctggttc   840
gcggacgagc  acccggtgga  cgccgccttc  gtgaccaaca  gcaccgtggc  cgacgagctc   900
gggcgccgca  cgcgcgtctc  cgtggtgaac  gtgacgcgcg  cggacgtccc  gggcctcgcg   960
gccgcggacg  acgcggacgc  gctcgcgccg  agcctgcgct  gcgaggccgt  gtggtaccgc  1020
gacagcgtgg  cctcgcagcg  cttctccgag  gccctgcgcc  cccacgtcta  ccacccggcg  1080
gcggtctcgg  tgcgcttcgt  cgagggcttc  gccgtctgcg  acggcctctg  cgtgcccccg  1140
gaggcgcgcc  tcgcctggtc  cgaccacgcc  gccgacaccg  tctaccacct  cggcgcctgc  1200
gccgagcacc  ccggcctgct  caacgtgcgg  agcgcccgcc  cgctgtcgga  cctcgacggg  1260
cccgtcgact  acacctgccg  cctcgagggc  atgccctcgc  agctgcccat  cttcgaggac  1320
acgcagcgct  acgacgcctc  ccccacgtcc  gtgagctggc  ccgtcgtgac  cagcatgatc  1380
accgtcatcg  ccggcatcgc  catcctagcc  atcgtgctgg  tcatcatggc  gacgtgcgtc  1440
tactaccgcc  gggcgggggcc  gtga                                          1464
```